United States Patent [19]

Lieber et al.

[11] 4,329,993

[45] May 18, 1982

[54] CATHETER WITH TRANS-LUMINAL ELECTRICAL CONDUCTOR

[75] Inventors: Clement E. Lieber; Robert P. Cooper, both of Yorba Linda; Michael S. Estes, Irvine, all of Calif.

[73] Assignee: American Hospital Supply Corporation, Evanston, Ill.

[21] Appl. No.: 160,600

[22] Filed: Jun. 18, 1980

[51] Int. Cl.³ ............................................. A61M 25/00
[52] U.S. Cl. ................................. 128/349 B; 128/691
[58] Field of Search ................... 128/349 B, 642, 673, 128/675, 692, 713, 715, 768, 786

[56] References Cited

U.S. PATENT DOCUMENTS

| | | | |
|---|---|---|---|
| 3,359,974 | 12/1976 | Khalil | 128/713 |
| 3,448,739 | 6/1969 | Stark et al. | 128/673 |
| 3,499,435 | 3/1970 | Rockwell et al. | 128/696 |
| 3,707,960 | 1/1973 | Freed | 128/642 |
| 3,951,136 | 4/1976 | Wall | 128/642 |
| 3,995,623 | 12/1976 | Blake et al. | 128/768 |

*Primary Examiner*—William E. Kamm
*Attorney, Agent, or Firm*—Tilton, Fallon, Lungmus

[57] ABSTRACT

A catheter having at least two separate lumens, one containing a gas required in connection with the operation of a pressure responsive element adjacent the catheter's distal end and the other for conveying liquid to and from a port spaced proximally from the pressure responsive element. The two lumens are separated by a longitudinal septum and combine to perform a third function—that of enclosing an electrical conductor which extends through that portion of the gas-containing lumen proximal to the port and through that portion of the liquid-conveying lumen beyond the port. The conductor switches from one lumen to the other through a sealed aperture in the septum. A method of forming such a catheter is also disclosed.

6 Claims, 9 Drawing Figures

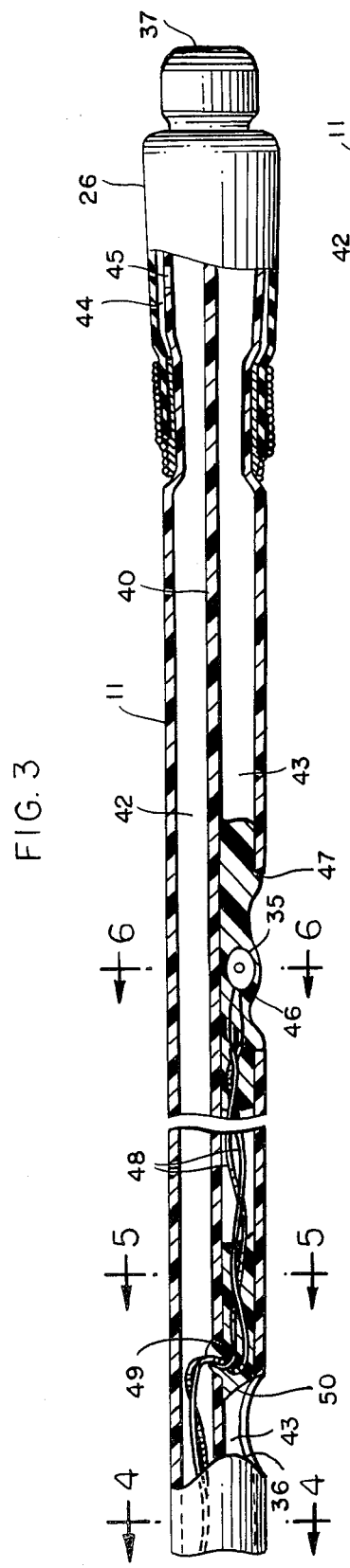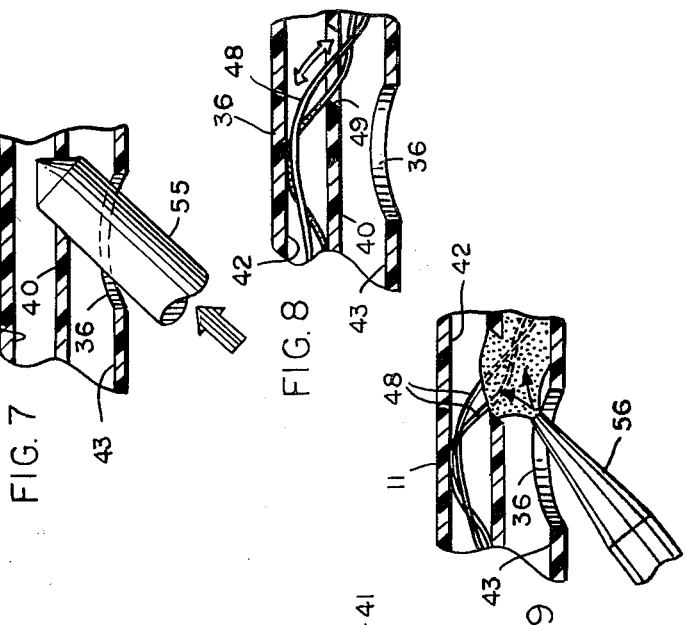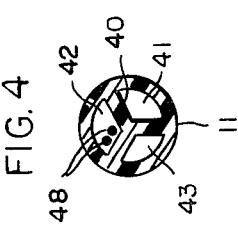

CATHETER WITH TRANS-LUMINAL ELECTRICAL CONDUCTOR

BACKGROUND

U.S. Pat. No. 3,995,623 discloses a multi-lumen flow-directed catheter suitable for use in diagnosing cardiovascular and pulmonary diseases. When the catheter is used for thermodilution measurements, a bolus of cold liquid is injected into the right atrium or superior vena cava (through port 30) and the resultant change in blood temperature is detected by a thermistor (represented by numeral 35) in the pulmonary artery, such change in blood temperature being representative of cardiac output. Three lumens are required by the patented construction to achieve such operation, one lumen conducting gas for balloon inflation, another conveying liquid for the injection of the cold bolus (or for right atrium pressure monitoring, blood sampling, or infusion of therapeutic media) and a third carrying the thermistor leads. One or more additional lumens would be provided where further capabilities are desired; thus, the patent discloses a fourth lumen (C) which extends completely through the catheter body for use in measuring pulmonary arterial pressures when the catheter is in place and the balloon is deflated, or pulmonary capillary wedge pressures when the balloon is inflated.

While the multiple function capability is an important objective, especially for heart catheterization where it is desirable to obtain as much diagnostic information as possible in a single catheterization procedure, such an objective has been achieved in the past either by increasing the size (outside diameter) of such a catheter or by reducing the cross section of each lumen and, hence, lowering the performance characteristics of the catheter. Not only must the lumens be made smaller, if their number is to be increased without altering the catheter's outside dimensions, but the necessity of providing septa between the lumens requires a further reduction in lumen size. Even when the partitions or septa which define the multiple lumens are made as thin as possible, their thickness still substantially reduces the space available for the several lumens within a catheter of any given size. At the same time, the outside dimensions of such a catheter, which must be capable of passing through the vascular system without injury to the patient, must be kept as small as possible. A 4 French catheter (approximately 0.053 inch O.D.) would therefore generally be considered more desirable than a larger 6 French (0.078 inch O.D.) catheter in terms of ease of manipulation and reduced risk of possible complications in use. Consequently, in order to achieve multiple functions in a cardiac catheter of optimum size, it has generally been considered necessary to compromise the performance capabilities of such a catheter.

Other patents disclosing multiple-lumen catheters are U.S. Pat. Nos. 3,746,003, 3,833,004, 3,710,781, 3,634,924, 3,152,592, 3,044,468, 3,050,066, and 2,845,930.

SUMMARY

This invention lies in part in the discovery that prior concepts requiring that the electrical leads of a catheter must be isolated in a separate lumen, in order to avoid liquid contact and electrical shorting and their attendant risks for patients, are not entirely valid. Specifically, applicants have discovered that in the construction of a catheter requiring a gas-transmitting passage, such as a flow-directed balloon catheter, and also requiring a proximal port for cold bolus introduction (or for blood sampling or pressure measurements) and a distal thermistor or other electrical element, one of the lumens previously thought to be necessary may be omitted completely. Since the space which such a lumen would have occupied may be used to increase the cross sectional dimensions of other lumens, and since the space which would have been occupied by a septum needed for the purpose of defining such a lumen also becomes available, the result is that a catheter made in accordance with this invention would have superior flow capacity and other performance characteristics when compared with a conventional catheter of similar outside dimensions. Viewed differently, the present invention makes it possible to reduce substantially the outside dimensions of a plural-lumen catheter without at the same time reducing its performance characteristics.

Such objectives have been achieved by eliminating the lumen which would normally carry the electrical leads and by extending those leads through portions of other lumens in such a way that the leads are nevertheless isolated from possible liquid contact. In the disclosed construction, the leads or conductors extend through the gas-conducting lumen from the proximal end of the catheter to an intermediate point, at which point such leads pass through the longitudinal septum separating the gas-conducting lumen from a second lumen used for bolus injection and other diagnostic functions. The leads then continue through the second lumen to a distal point where an electrical element, ordinarily a thermistor or other sensor, is located. Liquid cannot enter that portion of the second lumen containing the electrical leads because the port for bolus discharge (or for liquid sampling or atrial pressure measurements) is isolated from the aperture and the electrical leads extending therethrough by a sealant plug which embeds the leads at the point of traverse and which blocks flow communication between the proximal portion of the second lumen and the distal portion of the same lumen.

In practicing the method of the invention, a lateral port is first formed in the outer wall of the catheter body at an intermediate point, the port being located so that it communicates only with the lumen of the catheter intended to convey liquid for bolus injection, blood sampling, or pressure measurements. A suitable tool is then inserted through the port to form an aperture in the septum which separates the lumen for liquid flow from a parallel lumen intended to carry only gas, such as gas intended for balloon inflation and deflation. The aperture is preferably formed just distal to the port, a procedure which may be readily accomplished by inserting the tool through the port at an angle so that the tip of the tool pierces the septum at a distally-offset point. At least one electrical conductor is then threaded through the catheter body so that the proximal portion of the electrical lead is disposed in the gas-conducting lumen on the proximal side of the aperture, a distal portion of the lead extends through the other lumen on the distal side of the aperture, and an intermediate portion of the lead extends through the aperture from one lumen to the other. Finally a sealant plug is introduced into the second lumen through the port to close and seal a portion of the liquid-carrying lumen just distal to the port and, preferably, to also seal the aperture in the septum, while maintaining an open gas-conducting lumen. In the embodiment shown, the sealant also embeds the intermediate portion of the lead and any part of the distal portion of that lead that might otherwise be exposed to fluids passing through the port to the proximal end of the catheter body.

Other objects and advantages of the invention will be apparent from the specification and drawings.

DRAWINGS

FIG. 3 is an enlarged broken longitudinal sectional view of the distal portion of the catheter.

FIG. 4 is a cross sectional view taken along line 4—4 of FIG. 3.

FIG. 5 is an enlarged cross sectional view taken along line 5—5 of FIG. 3.

FIG. 6 is an enlarged cross sectional view taken along line 6—6 of FIG. 3.

FIGS. 7 through 9 are somewhat schematic views illustrating a sequence of steps in performing the method of the invention.

DETAILED DESCRIPTION

Figure 1:
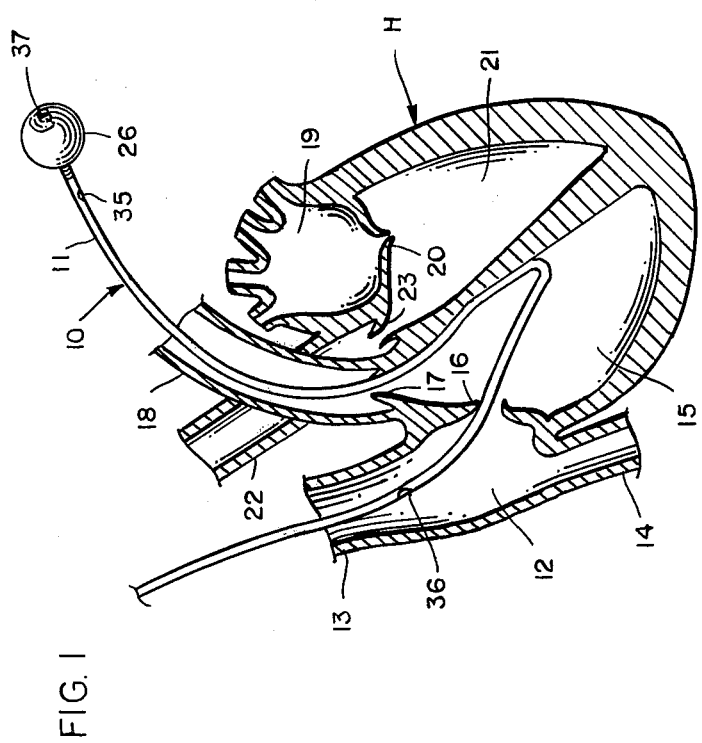
FIG. 1 is a somewhat diagrammatic sectional view illustrating a flow-directed catheter embodying this invention when such a catheter is positioned for use.

FIG. 1 illustrates a catheter 10 extending through the right side of a patient's heart H. In brief, the parts of the heart and their operation are as follows: the right atrium 12 receives blood from the superior and inferior vena cava veins 13 and 14 and pumps such blood into the right ventricle 15 through tricuspid valve 16. From the right ventricle, the blood travels to the lungs through pulmonary valve 17 and pulmonary artery 18. Oxygenated blood returning from the lungs enters left atrium 19 and then passes through mitral valve 20 into right ventricle 21. The blood leaves the heart through aorta 22 after passing through aortic valve 23.

Catheter 10 is depicted as a multiple-purpose flow-directed catheter having a tubular body 11 equipped at its distal end with pressure responsive means in the form of a balloon 26. At its proximal end, the catheter body terminates in a coupling 27 which operatively connects the lumens of the catheter to connector tubes 28, 29, and 30. Connector 29 bifurcates to provide branches 29a and 29b and, as well known in the art, all of the tubes or branches are provided with coupling elements 31–34 for attaching the connector tubes to syringes or other devices.

The structure so far described is essentially conventional. In use, the soft, pliable catheter body is introduced into the vascular system from the antecubital, femoral, subclavian, or jugular areas and is advanced, with the balloon in deflated or only partially inflated condition, into the right atrium 12. The balloon is then inflated to its maximum recommended capacity and the flow of blood through the heart rapidly propels the inflated balloon-tipped catheter from the right atrium into the pulmonary artery 18 (FIG. 1). It will be observed that when the catheter is so positioned, balloon 26 has advanced through the pulmonary artery into what is generally referred to as the pulmonary capillary wedge position, a sensor or other electrical element 35 at the distal end portion of the catheter body (just proximal to the balloon 26) is disposed within the pulmonary artery, and a lateral flow port 36, sometimes referred to as a proximal port (in contra distinction to distal port 37 at the tip of the catheter body distal to the balloon) is positioned within right atrium 12. With the catheter so positioned, a variety of diagnostic procedures may take place, all of which are well known and, therefore, will be described only briefly here. Port 36 may be used for taking pressure measurements from the right atrium, for injecting or infusing solutions, or for taking blood samples, whereas distal port 37 may also be used for sampling, infusion or injection, or measuring pulmonary artery and pulmonary capillary wedge pressures (depending on whether such measurements are taken with balloon 26 inflated or deflated). In thermodilution measurements, a sterile, cold solution is injected into the right atrium through port 36 and the resulting change in blood temperature is detected by thermistor 35, thereby allowing calculation of cardiac output.

It is to be understood that the electrical element 35 need not take the form of a thermistor; it may, for example, be an electrode for sensing (or, if necessary, stimulation) electrical activity of the heart as disclosed in detail in co-owned U.S. Pat. No. 3,995,623. However, unlike the construction disclosed in that patent, which has four lumens extending through the catheter body, the catheter of the present invention is capable of performing the same functions with only three lumens.

As shown in FIG. 4, catheter body 11 is divided by a three-branched partition or septum 40 so that it defines three parallel lumens 41, 42, and 43. Lumen 41 is a through lumen which communicates with connector tube 28 and which extends all of the way to distal port 27. Such a lumen is illustrated because of the functions already described with which such distal port is associated; if such functions are regarded as unnecessary, then it is to be understood that through lumen 41 may be eliminated and the space that would otherwise be occupied by that lumen may be used for increasing the size of lumens 42 and 43, or for providing a lumen intended to perform some other purpose, or for reducing the outside cross sectional dimensions of the catheter body.

Lumen 42 is a passage which communicates with connector tube 29 and which conveys gas to and from balloon chamber 44 for inflating and deflating balloon 26. The gas of choice is carbon dioxide because of its relatively rapid diffusion rate in blood should the balloon rupture; however, it is conceivable that other gases might be used or even recommended under special circumstances. Furthermore, while a balloon is represented in the drawings and described in detail herein for purposes of illustration, it is to be understood that other types of pressure responsive means might be substituted. For example, the pressure responsive means might take the form of a diaphragm-equipped pressure transducer for measuring blood pressure at or near the tip of the catheter, the lumen 42 in such a case serving as a gas-containing passage for venting the opposite side of the diaphragm to atmosphere.

Where the pressure responsive element 26 comprises a balloon, the gas enters and leaves the balloon chamber through a lateral port 45 formed in the wall of catheter body 11 (FIG. 3). The balloon 26 may be secured in place in any suitable manner, reference being made to U.S. Pat. Nos. 3,995,623, 3,746,003, and 3,833,004 for further information in that regard. Since balloon-attachment methods and constructions are well known in the art and form no part of the present invention, a more detailed description is believed unnecessary herein. It should be noted, however, that the balloon is shown in its fully deflated condition in FIG. 3 and FIG. 2 (solid lines) and in fully inflated condition in FIG. 1 and in FIG. 2 (phantom lines).

Figure 2:
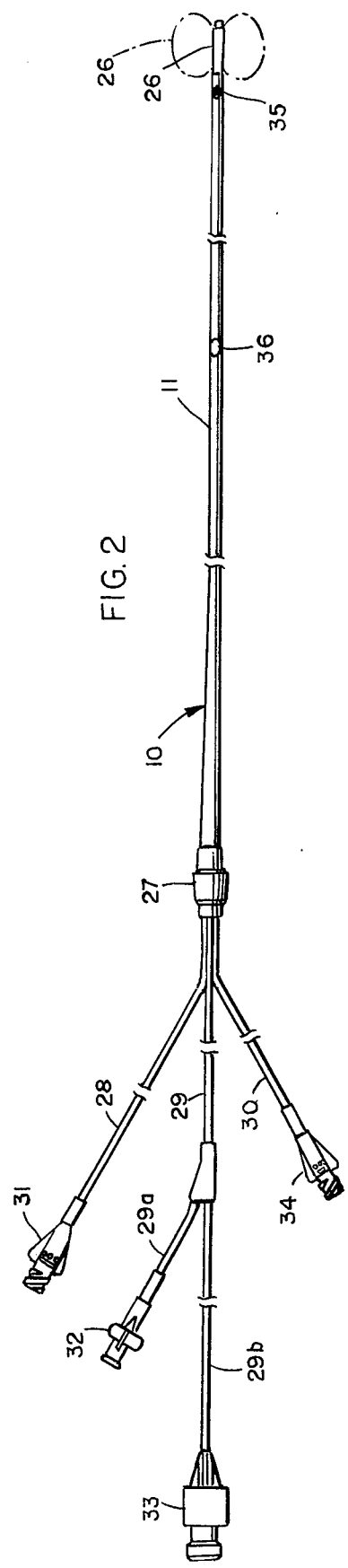
FIG. 2 is a side elevational view of the catheter.

Lumen 43 is the lumen which carries liquids to or from proximal port 36. As indicated, that port is so named because it is a substantial distance from the tip of the catheter and from distal port 37; however, as shown in FIG. 2, port 36 is actually located in an intermediate position. Thus, in a typical catheter having a total body length of approximately 110 centimeters, the distance between the proximal lumen and the distal tip would ordinarily fall within the range of approximately 15 to 35 centimeters, such distance being selected so that, when the catheter is positioned as shown in FIG. 1, port 36 will be disposed in the right atrium or superior vena cava.

Electrical element 35 is located within lumen 43 near balloon 26. As shown most clearly in FIG. 3, the electrical element, which takes the form of a thermistor, is embedded in a suitable embedding medium 46 adjacent an opening 47 formed in the outer wall of the catheter body. While any appropriate embedding medium may be used particularly effective results have been obtained with a polyurethane casting material marketed by N. L. Chemicals, Heightstown, New Jersey, under the designation "Biothane."

The leads or wires 48 for the electrical element extend proximally through lumen 43 to a point adjacent, and preferably just distal to, port 36. At that point, the leads extend transversely through an aperture 49 in the septum 40 which separates lumen 43 from lumen 42. The leads then continue in a proximal direction through lumen 42, extending into connector tube 29, branch 29b, and coupling 33. As is well known, coupling 33 may be connected to a thermodilution cardiac output computer or, should element 35 take the form of an electrode rather than a thermistor, to other appropriate electronic equipment.

A sealant plug 50 is located in lumen 43 on the distal side of port 36 and performs the multiple functions of sealing the distal portion of lumen 43 against the ingress of liquid, closing aperture 40 so that fluids cannot pass between lumens 42 and 43, and embedding leads 48 in the vicinity of port 36 so that such leads are not exposed to liquids passing through that port. If the catheter body is formed of polyvinyl chloride, then a sealant plug composed of polyvinyl chloride has been found effective; however, it is to be understood that any of a variety of materials may be selected for the catheter body and for the sealant plug.

From the foregoing, it is believed apparent that the catheter of the present invention requires one less lumen than prior catheters to achieve the same monitoring or diagnosing functions, and that the elimination of one lumen permits size adjustments which result in either improved performance characteristics, or smaller external size, or both. For example, it has been found that a three-lumen catheter of the present invention of 4 French size has performance characteristics (flow capacity and frequency response) approximating those of a substantially larger (outside diameter) prior art four-lumen catheter of size 6 French.

The wires or leads 48 for electrical element 35 are insulated although such insulation is intended primarily to prevent the conductors from making electrical contact with each other since the sealant plug 50 so effectively prevents liquid from invading lumen 42 or from contacting the leads. The leads are also protected against contact with blood that might enter lumen 42 through inflation port 45 should balloon 26 rupture in use because blood entering that lumen would clot and seal the lumen long before reaching leads 48 at the crossover point.

Certain steps of fabricating the catheter are illustrated in FIGS. 7 through 9. After the proximal port 36 has been formed in the catheter body at a point intermediate its length, an aperture-forming tool 55 is inserted at a forwardly-directed angle through port 36 and into contact with septum 40 (FIG. 7). The tool or probe may be heated to cause the thermoplastic material of septum 40 to melt upon contact and thereby develop aperture 49, although it is believed apparent that other cutting or piercing techniques may be used to form that aperture. It will be observed that the aperture 49 is smaller than the port 36, the latter serving as an access port during the fabrication procedure, and that the aperture is formed on the distal side of the port.

After aperture 49 has been formed, any desired number of electrical conductors 48 are drawn into position (FIG. 8). When that step is completed, each conductor has a proximal portion disposed in lumen 42 on the proximal side of aperture 49, an intermediate portion extending through the aperture, and a distal portion in lumen 43 on the distal side of aperture 49. Sealant plug material is introduced from a nozzle 56 into lumen 43, again using port 36 as an access opening (FIG. 9). Upon solidification, the sealant forms the final plug 50 which embeds those portions of leads 48 adjacent port 36 and which seals aperture 49 and lumen 43 just distal to proximal port 36. Preferably, the trailing surface of plug 50 is contoured as shown in FIG. 3 to help direct the flow of liquid exiting port 36 (and discharged from a syringe connected to coupling 34 and connector tube 30) or entering that port for the taking of samples or pressure measurements. In the case of pressure measurements, it is to be understood that couplings 37 and/or 34 would be connected to any of a variety of pressure measuring devices rather than to syringes.

In the illustrated embodiment, the sealant plug is formed in situ, being introduced into the lumen in fluid form by means of nozzle 56. It is to be understood that, if desired, the plug may be introduced into the lumen in pre-formed condition. Such a pre-formed plug may be provided with a recess or passage to accommodate those portions of the lead wires immediately adjacent aperture 49 within lumen 43, thereby optionally permitting location of the aperture within the axial limits of port 36. Whether pre-formed or not, the sealant plug, when secured in place within lumen 43, performs the multiple functions of isolating the lead wires and the gas flow path from liquid passing into or out of the proximal portion of lumen 43 through port 36.

While in the foregoing, we have disclosed an embodiment of the invention in considerable detail for purposes of illustration, it will be understood by those skilled in the art that many of these details may be varied without departing from the spirit and scope of the invention.

We claim:

1. A catheter comprising a catheter body having an elongated tubular wall formed of flexible material and having proximal and distal ends; pressure responsive means mounted upon said body adjacent the distal end thereof; said body having a first lumen extending from said proximal end to said distal end and communicating with said pressure responsive means for exposing said means to gas pressure within said first lumen; said body also having a second lumen parallel with said first lumen and having a longitudinal septum separating said first and second lumens; a port in said wall of said body communicating with said second lumen and being located intermediate said distal and proximal ends; an aperture in said septum; at least one electrical lead extending through the portion of said first lumen proximal to said aperture and through said aperture into the portion of said second lumen distal to said aperture; electrical means mounted upon said catheter distal to said port and connected to said lead; and a sealant plug means disposed within said second lumen and providing a fluid-tight barrier within the second lumen on the distal side of said port to block liquid from entering the portion of said second lumen distal to said port and from entering said first lumen through said aperture.

2. The catheter of claim 1 in which said electrical means is a sensor for sensing a condition of a body into which said catheter is inserted.

3. The catheter of claim 1 in which said aperture is adjacent to said port on the distal side thereof and said plug means embeds that portion of said lead extending through said aperture and into the portion of said second lumen distal to said port to prevent contact between said lead and liquid flowing through said port.

4. The catheter of claim 3 in which said aperture is smaller than said port.

5. The catheter of claim 1 in which said port is spaced from the distal end of said catheter a distance within the range of 15 to 35 centimeters.

6. The catheter of claims 1, 2, 3, 4, or 5 in which said pressure responsive means is an inflatable balloon, said catheter body having an opening in the wall thereof communicating with both said balloon and said first lumen.

* * * * *